US00PP16899P3

(12) United States Plant Patent
Lintott

(10) Patent No.: US PP16,899 P3
(45) Date of Patent: Aug. 1, 2006

(54) ***CHRYSANTHEMUM* PLANT NAMED 'STARLET PINK'**

(50) Latin Name: *Chrysanthemum morifolium*
Varietal Denomination: Starlet Pink

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 148 days.

(21) Appl. No.: 10/693,739

(22) Filed: Oct. 24, 2003

(65) Prior Publication Data

US 2004/0107471 P1 Jun. 3, 2004

Related U.S. Application Data

(60) Provisional application No. 60/421,387, filed on Oct. 25, 2002.

(51) Int. Cl.
*A01H 5/00* (2006.01)

(52) U.S. Cl. ..... Plt./297

(58) Field of Classification Search ..... Plt./297
See application file for complete search history.

(56) References Cited

PUBLICATIONS

Royal Van Zanten Garden Mum Catalog 2002 listing *Chrysanthemum* variety 'Starlet Pink' at pp. 5 (color picture), 9 and 14. The variety 'Dove' is also listed in the catalog at p. 5 (color picture), 9 and 14.

*Primary Examiner*—Anne Marie Grunberg
*Assistant Examiner*—Annette H Para
(74) *Attorney, Agent, or Firm*—Winston & Strawn LLP

(57) ABSTRACT

A new variety of *Chrysanthemum* plant named 'Starlet Pink,' having a uniform domed and round habit. The new variety produces a uniform canopy of small pink single flowers and good foliage.

1 Drawing Sheet

Latin name of the genus and species: Botanical classification: *Chrysanthemum morifolium.*

Variety denomination: The new *Chrysanthemum* variety denomination is 'Starlet Pink.'

BACKGROUND OF THE INVENTION

The present invention comprises a new and distinct cultivar of *Chrysanthemum* botanically known as *Chrysanthemum morifolium,* and referred to by the cultivar name 'Starlet Pink.'

'Starlet Pink,' identified as 30912-0, originated from a cross made in a controlled breeding program in Chichester, West Sussex, United Kingdom. The female parent of the new variety is an undistributed, unpatented seedling identified as 'G15E2.' The male parent of the new variety is the unpatented variety known as 'Leyla.' The new variety 'Starlet Pink' has been asexually reproduced by vegetative cuttings in Chichester, West Sussex, United Kingdom and the distinguishing characteristics are retained through successive generations of asexual reproduction.

BRIEF SUMMARY OF THE INVENTION

'Starlet Pink' is a garden type of *Chrysanthemum* plant variety having a domed-round habit carrying a uniform canopy of small pink single flowers.

Comparison with Female Parent

Plants of the new *Chrysanthemum* variety 'Starlet Pink' are similar to the parent variety 'G15E2' in plant habitat and growth rate. In side-by-side comparisons in Chichester, West Sussex, United Kingdom, under commercial practice, plants of the new *Chrysanthemum* variety 'Starlet Pink' differed from plants of the parent 'G15E2' in the following characteristics.

1. The new variety 'Starlet Pink' produces pale pink flowers whereas the parent 'G15E2' produces purple flowers.
2. Plants of the new variety 'Starlet Pink' have a more domed and round habit than plants of the parent 'G15E2.'
3. Flowers of the new variety 'Starlet Pink' are larger than flowers of the parent variety 'G15E2.'

Comparison with Male Parent

Plants of the new *Chrysanthemum* variety 'Starlet Pink' are similar to the parent 'Leyla' in plant habitat and growth rate. In side-by-side comparisons in Chichester, West Sussex, United Kingdom, under commercial practice, plants of the new *Chrysanthemum* variety 'Starlet Pink' differed from plants of the parent 'Leyla' in the following characteristics.

1. The new variety 'Starlet Pink' produces pale pink flowers whereas the parent 'Leyla' produces yellow flowers.
2. Plants of the new variety 'Starlet Pink' have a more round domed habit than plants of the parent 'Leyla.'
3. Plants of the new variety 'Starlet Pink' are less vigorous than plants of the parent 'Leyla.'

Comparison with Other Varieties

Plants of the new *Chrysanthemum* variety 'Starlet Pink' are dissimilar to the unpatented but distributed variety 'Dove' in plant habit and growth rate. In side-by-side comparisons in Chichester, West Sussex, United Kingdom, under commercial practice, plants of the new *Chrysanthe-*

*mum* variety 'Starlet Pink' differed from plants of the variety 'Dove' in the following characteristics.

1. The new variety 'Starlet Pink' produces pale pink flowers whereas 'Dove' produces deeper pink flowers.
2. Plants of the new variety 'Starlet Pink' have shorter and less inflorescence than plants of the variety 'Dove.'
3. Plants of the new variety 'Starlet Pink' are less vigorous than plants of the variety 'Dove.'

BRIEF DESCRIPTION OF ILLUSTRATION

Typical specimens of the plant and flowers for the new *Chrysanthemum* variety 'Starlet Pink' are shown in the accompanying digital photograph. The colors shown are as true as possible within the usual limits of this kind of illustration.

FIG. 1 is a whole plant view of the new variety 'Starlet Pink' grown in a pot. The plant shown in the illustration is 70 days from the commencement of planting outdoors in mid-June.

DETAILED BOTANICAL DESCRIPTION

The following description of the new *Chrysanthemum* variety 'Starlet Pink' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 65° F. to 75° F. during the day under natural light conditions. The plants were grown outdoors in mid-June in 4 liter pots using a loamless compost. No growth retardants were used. To produce a commercial product the plants may be pinched once with the center bud removed. The typical container size for commercial growth is 4 liter (8"). It has been observed that the shelf life of the new variety is about 25 days with a response time of about 10 weeks natural season. The new variety is suitable for growth in a temperature range of 50° F. to 75° F.

The new variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed-Round.
Height: 50 cm.
Width: 50 cm.
Branching characteristics: Free Branching.
Length of lateral branches: 14–27 cm.
Number of breaks from pinch: 7–11.
Stem color: Near 137A.
Response time: 70 days natural season.
Vigor: Medium.
Shelf life: 25 days.
Disease (susceptibility/resistance observed): None observed to date.
Pest (susceptibility/resistance observed): None observed to date.
Growth retardant type and treatment: No treatment necessary.

The plants were grown for 10 weeks in natural season conditions.

Propagation:
*Type.*—Vegetative via Stem Cuttings.
*Time to rooting.*—12 days with soil temperatures of 70° F.
*Rooting habit.*—Fine and Fibrous.

Foliage

Number of leaves per lateral branch: 8–10.
Compound or single: Single.
Arrangement of leaves: Alternate.
*Shape of leaf.*—Typically 5 lobed ovate.
*Size of leaf.*—Width (cm): 1–1.5. Length (cm): 2–4.
*Leaf apex.*—Rounded.
*Base.*—Cordate.
*Attachment.*—Petioled.
*Aspect.*—Slightly Undulating.
*Margin.*—Palmately Lobed.
*Surface characteristics.*—Top: Slightly Pubescent. Bottom: Slightly Pubescent.
Petiole:
*Color.*—Near 138B.
*Length.*—0.8–1.2 cm.
Venation: Net prominent mid vein at underside.
*Color.*—Upper side: near 136B. Under side: near 136C.
Color:
*Mature leaf, upper side.*—Near 137A; under side: near 137C.
*Young leaf, upper side.*—Near 137A; under side: near 137C.

Flower

Flower appearance: Matte.
Flower type: Single.
Flower form: Flat.
Flower shape: Round.
Flowering habit: Cyme.
Number of blossoms per branch: 12–15.
Inflorescence form: Corymibiform.
*Depth of fully expanded blossoms.*—1 cm.
*Diameter of fully expanded blossoms.*—2.5–3.5 cm.
Phyllaries:
*Number.*—23–25.
*Color.*—Near 138A.
*Length.*—4–7 mm.
*Width.*—1–1.5 mm.
*Texture/appearance.*—Pubescent.
Pedical:
*Length.*—Terminal: 8 cm; lateral: 11 cm.
*Color.*—Near 138B.
*Surface.*—Pubescent.
*Habit.*—Straight/Slightly Curving.
*Strength.*—Medium.
Ray florets:
*Form/shape.*—Straight.
*Texture/appearance.*—Matte.
*Number per flower.*—50–60.
*Length.*—1–1.5 cm; Width: 3–5 mm.
*Apex.*—Round.
*Base.*—Tubular.
*Margin.*—Entire.
Disc florets:
*Form/shape.*—Cylindrical.
*Texture/appearance.*—Shiny.
*Number per flower.*—130–150.
*Length.*—4–6 mm; Width <1 mm.
*Diameter of disc.*—1.2 cm.

Fragrance: None observed.
Flower bud (at onset of color):
*Length.*—1 cm.
*Diameter.*—0.8–1 cm.
*Form/shape.*—Globular.
General flower color:
1. *Ray florets, upper side.*—Immature: near 55C. Mature: near 36D. Older/Fading: near 36D.
2. *Ray florets, under side.*—Immature: near 55C. Mature: near 36D. Older/Fading: near 36D.
3. *Disc florets.*—Immature: near 7A. Mature: near 17B. Older/Fading: near 17C.
4. *Bud.*—39A.

Flower progression with age: Flower color deepens uniformly with age and the flowers become slightly cupped shape.

Reproductive Organs

Gynoecium present on ray and disc florets.
Ray florets per individual flower:
*Pistil number.*—35–40 observed.
*Stigma color.*—Near 144D.
*Stigma shape.*—Forked.
*Style color.*—Near 144D.
*Style length.*—1–2 mm.
Disc florets per individual flower:
*Pistil number.*—120–130.
*Stigma color.*—144D.
*Stigma shape.*—Forked.
*Style color.*—Near 144D.
*Style length.*—2 mm.
Androecium present on disc florets only.
*Stamen number.*—20–25 observed.
*Anther shape.*—Ovoid.
*Anther color.*—Near 14C.
*Pollen color.*—Near 12A.
*Pollen quantity.*—Slight.
Fruit and seeds: None observed.

What is claimed is:

1. A new and distinct variety of *Chrysanthemum* plant, substantially as described and illustrated herein.

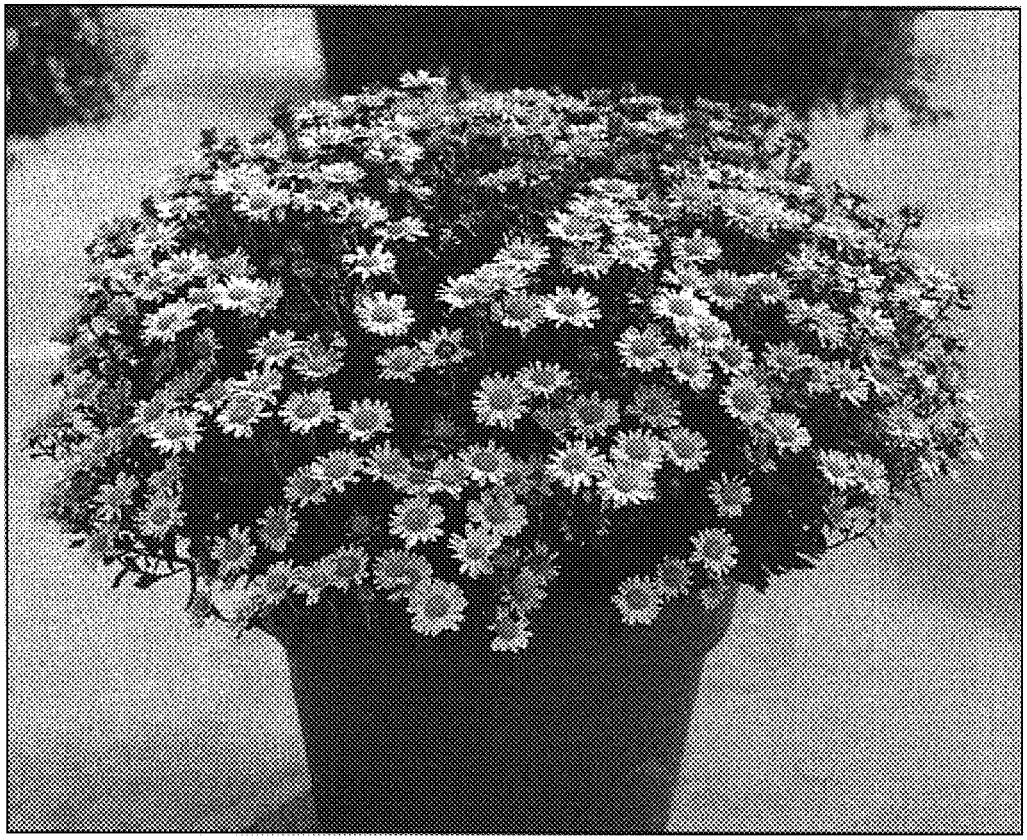

* * * * *